(12) United States Patent
Fletcher et al.

(10) Patent No.: US 10,737,093 B2
(45) Date of Patent: Aug. 11, 2020

(54) WEARABLE ITEM FOR INCREASED APPLICATION OF NUTRIENTS

(71) Applicant: The Vitasken Venture Club, Dover, DE (US)

(72) Inventors: Keith Fletcher, Denver, CO (US); Joel Greco, Lone Tree, CO (US)

(73) Assignee: The Vitasken Venture Club, Dover, DE (US)

( * ) Notice: Subject to any disclaimer, the term of this patent is extended or adjusted under 35 U.S.C. 154(b) by 950 days.

(21) Appl. No.: 14/790,962

(22) Filed: Jul. 2, 2015

(65) Prior Publication Data

US 2016/0001069 A1    Jan. 7, 2016

Related U.S. Application Data

(60) Provisional application No. 62/188,251, filed on Jul. 2, 2015, provisional application No. 62/083,758, filed on Nov. 24, 2014, provisional application No. 62/020,851, filed on Jul. 3, 2014.

(51) Int. Cl.
| | | |
|---|---|---|
| *A61N 1/30* | (2006.01) | |
| *A61B 5/00* | (2006.01) | |
| *A61N 1/04* | (2006.01) | |
| *A61N 1/372* | (2006.01) | |

(52) U.S. Cl.
CPC ............ *A61N 1/303* (2013.01); *A61B 5/6804* (2013.01); *A61B 5/7435* (2013.01); *A61N 1/0412* (2013.01); *A61N 1/0484* (2013.01); *A61N 1/37247* (2013.01)

(58) Field of Classification Search
CPC .... A61N 1/303; A61N 1/0412; A61N 1/0484; A61N 1/37247; A61N 1/325; A61N 1/327; A61B 5/7435; A61B 5/6804; B32B 2307/202; G06F 3/044
See application file for complete search history.

(56) References Cited

U.S. PATENT DOCUMENTS

| | | | | |
|---|---|---|---|---|
| 6,048,545 | A * | 4/2000 | Keller | A61K 9/0009 424/1.21 |
| 2011/0276112 | A1 * | 11/2011 | Simon | A61N 1/40 607/72 |
| 2013/0274587 | A1 * | 10/2013 | Coza | A61B 5/6804 600/409 |
| 2015/0257543 | A1 * | 9/2015 | Baxter | A47C 27/002 5/706 |

* cited by examiner

*Primary Examiner* — Nathan R Price
*Assistant Examiner* — Justin L Zamory
(74) *Attorney, Agent, or Firm* — Faegre Drinker Biddle & Reath LLP

(57) ABSTRACT

A wearable item is formed of conductive fibers and non-conductive fibers. Encapsulated nutrients are placed on the non-conductive fibers. A voltage is placed on the conductive lines in order to induce an electric field so that the effective absorption rate of the nutrients through the skin of a user is increased.

20 Claims, 19 Drawing Sheets

| | BAMBOO CELLOUSE FIBER | 304 |
| | SILVER FIBER | 306 |
| | ENCAPSULATED VITAMINS | 302 |

…

WEARABLE ITEM FOR INCREASED APPLICATION OF NUTRIENTS

CROSS REFERENCE TO RELATED APPLICATIONS

The present application claims the benefit of and priority to, under 35 U.S.C. § 119(e), U.S. Provisional Application Ser. No. 62/020,851, filed Jul. 3, 2014, entitled WEARABLE ITEM FOR INCREASED APPLICATION OF NUTRIENTS, U.S. Provisional Application Ser. No. 62/083,758, filed Nov. 24, 2014, entitled WEARABLE ITEM FOR INCREASED APPLICATION OF NUTRIENTS and U.S. Provisional Application Ser. No. 62/188,251, filed Jul. 2, 2015, entitled WEARABLE ITEM CAPABLE OF CHARGING, all of which are hereby incorporated herein by reference in their entireties for all that they teach and for all purposes.

TECHNICAL FIELD

Embodiments of the present invention generally relate to wearable items, such as shirts, that provide nutrients to a user transdermally, and specifically to wearable items that increase the effective absorption rate of vitamins applied transdermally.

BACKGROUND

Nutrients (e.g., vitamins) are important in ensuring a healthy lifestyle and can improve the performance of the human body. Nutrients generally enter the body orally and are absorbed by the blood stream via the digestive system. Various circumstances, however, can lead to a nutrient deficiency. Some examples include a lack of access to nutritional food and/or liquids, digestive disorders where nutrients are not properly absorbed by the digestive system, disorders that prohibit oral consumption of solid food and/or liquids, and exercise that depletes nutrients within the body. In these circumstances, and in others, replenishing nutrients via oral consumption of solid food and/or liquids may not be a viable and/or effective option.

SUMMARY

Embodiments of the present invention relate to the transdermal delivery of nutrients. In its typical state, the skin acts as a barrier against substances entering the body. The skin accomplishes this through the orderly arrangement of several cellular layers. At the same time, those cellular layers allow certain substances to pass through, a property referred to as selective permeability. In other words, certain substances are allowed to penetrate the skin while others are not. Factors that enable substances to cross the membrane (or that affect the rate at which certain substances cross the membrane) include size, electrical charge, and solubility of the substance in water versus in a lipid environment.

The process of electroporation, which in some embodiments is provided by the wearable item disclosed herein, acts to temporarily change the permeability of the lipid bilayer of the membrane of the stratum corneum, so that nutrients that previously could not enter the blood stream transdermally can now enter the bloodstream via transdermal application. Electroporation may also increase the rate at which other substances pass through the skin. As discussed in several of the examples below, a wearable item is configured to apply principles of electroporation in specific ways in order to increase the absorption rate of vitamins or other nutrients applied transdermally.

In Example 1, a wearable item for applying nutrients to a user comprises: a plurality of non-conductive fibers; nutrients embedded within the plurality of non-conductive fibers; and a plurality of conductive fibers interwoven with the plurality of non-conductive fibers, the plurality of conductive fibers being configured to apply an electric field to a portion of the skin of a user wearing the wearable item and thereby increase a permeability of the portion of the skin with respect to the nutrients.

In Example 2, the wearable item according to Example 1, wherein the nutrients are selected from a group consisting essentially of: water-soluble vitamins and fat-soluble vitamins.

In Example 3, the wearable item according to either Example 1 or 2, wherein the plurality of conductive fibers are arranged to form a Marx Generator to apply the electric field to the portion of the skin of the user wearing the item and thereby increase the permeability of the portion of the skin with respect to the nutrients.

In Example 4, the wearable item according to any of Examples 1-3, wherein the plurality of non-conductive fibers include at least one of the following: bamboo fibers, ramie fibers, hydrophobic cotton fibers or hydrophilic cotton cellulose fibers.

In Example 5, the wearable item according to any of Examples 1-4, wherein the nutrients include a first nutrient type and a second nutrient type, and the nutrients of the first nutrient type are embedded within a first region of the wearable item and the nutrients of the second nutrient type are embedded within a second region of the wearable item, wherein the first region is different than the second region.

In Example 6, the wearable item according to any of Examples 1-5, further comprising a processor-based nutrient applicator configured to selectively apply an electric field to the plurality of conductive fibers.

In Example 7, the wearable item according to any of Example 6, wherein the processor-based nutrient applicator is a removable dongle, and wherein the wearable item further comprises an interface configured to secure the removable dongle to the wearable item and to control a proximity of the removable dongle to the skin of the user.

In Example 8, the wearable item according to any of Examples 1-7, further comprising a visual indicator configured to convey information regarding an amount of nutrients coupled to the plurality of non-conductive fibers.

In Example 9, a removable dongle for increasing a permeability of a user's skin with respect to nutrients, the removable dongle comprising: an interface unit configured to removably couple the removable dongle to a wearable item; a nutrient applicator configured to provide nutrients to the user's skin; and a power application module configured to selectively apply an electric field to the user's skin to increase the permeability of the user's skin with respect the nutrients.

In Example 10, the removable dongle according to Example 9, wherein the nutrients are an array of nutrients including nutrients of a first type and nutrients of a second type, wherein the power application module is configured to selectively apply a first electric field to the user's skin to increase the permeability of the user's skin with respect to nutrients of the first type and to selectively apply a second electric field to the user's skin to increase the permeability of the user's skin with respect to nutrients of the second type.

In Example 11, the removable dongle according to either Example 9 or Example 10, wherein the removable dongle further comprises: a user interface configured to display a visual indicator of an amount of nutrients available to the nutrient applicator.

In Example 12, the removable dongle according to any of Examples 9-11, wherein the removable dongle further comprises: a user interface configured to display a visual indicator of an amount of energy available to the power application.

In Example 13, the removable dongle according to any of Examples 9-12, wherein the power application module is configured to receive energy from conductive fibers in the wearable item.

In Example 14, the removable dongle according to any of Examples 9-13, wherein the power application module is configured to selectively apply different electric fields to different portions of the wearable item using conductive fibers in the wearable item.

In Example 15, a system for improving the health and performance of a user, the system comprising: a wearable item formed of conductive fibers and non-conductive fibers and having nutrients embedded within non-conductive fibers, the conductive fibers forming a plurality of circuit elements; and a processor-based nutrient applicator configured to selectively generate an electric field, the processor-based nutrient applicator being further configured to selectively generate different electric field strengths at different regions of the wearable item using circuit elements of the plurality of circuit elements.

In Example 16, the system according to Example 15, wherein the processor-based nutrient applicator is further configured to receive user input and to selectively generate the electric field based on that user input.

In Example 17, the system according to either Example 15 or Example 16, wherein nutrients include a first nutrient type and a second nutrient type, and the nutrients of the first nutrient type are embedded within a first region of the wearable item and the nutrients of the second nutrient type are embedded within a second region of the wearable item, wherein the first region is different than the second region.

In Example 18, the system according to any of Examples 15-17, wherein the wearable item further includes power generating elements and wherein the processor-based nutrient applicator is configured to receive energy generated from the power generating elements.

In Example 19, the system according to Example 18, wherein the power generating elements include photovoltaic elements.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Figure 1A:
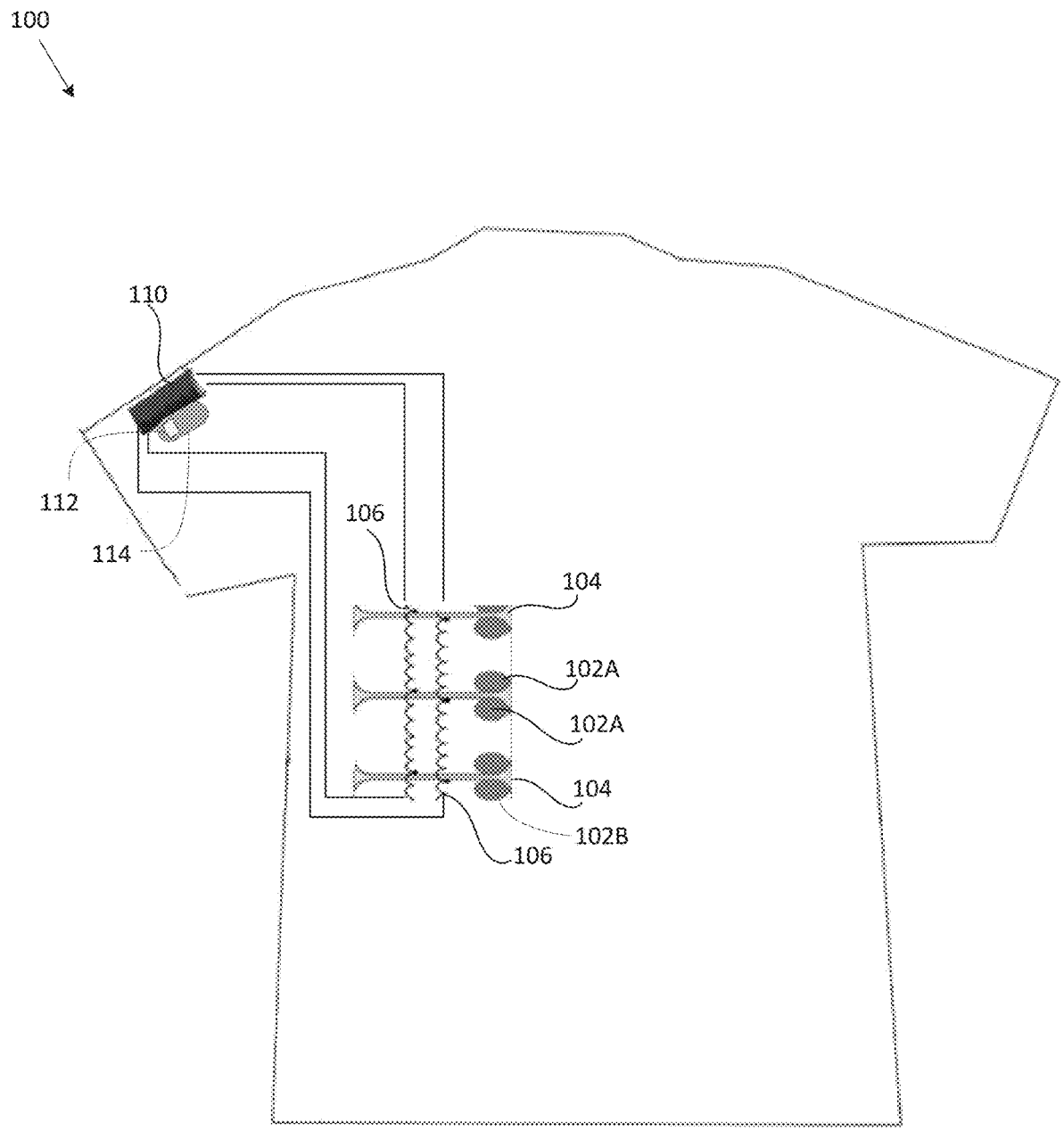
FIGS. 1A-1B illustrate exemplary wearable items, according to embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

According to embodiments disclosed herein, a wearable item provides the topical application of nutrients while increasing the effective absorption rate of those nutrients by using electroporation. Electroporation (or electropermeabilization) is an increase in the permeability of a cell membrane caused by an externally-applied electrical field.

FIG. 1A illustrates an exemplary wearable item 100 in accordance with embodiments of the present disclosure. The wearable item 100 delivers nutrients 102 transdermally using electroporation to different parts of the body (e.g., the surface of the torso, forehead, arms, legs, and the like). In particular, the wearable item comprises a plurality of non-conductive fibers 104; nutrients 102A, 102B embedded within the plurality of non-conductive fibers 104; and a plurality of conductive fibers 106 interwoven with the plurality of non-conductive fibers 104. The plurality of conductive fibers 106 are configured to apply an electric field to a portion of the skin of a user wearing the wearable item 100 and thereby increase the permeability of the portion of the skin with respect to the nutrients 102A, 102B. Furthermore, the wearable item 100 includes a power source 110 coupled to the conductive fibers 106, a dongle 114, and a processor-based nutrient applicator 112 that is incorporated in the dongle 114. The dongle 114 and the processor based nutrient application 112 control the electrical pulses, produced by the power source 110 and transmitted to the conductive fibers 106, which generate the electric field for electroporation. Each of these elements are discussed in detail below.

Once an electric field has been applied to the skin of the wearer of the wearable item 100, nutrients are more easily passed from the wearable item 100 into the blood stream of the user. In some embodiments, the wearable item 100 delivers nutrients 102A, 102B over a large surface area of the body (e.g., the majority or entirety of the torso). In other embodiments, the wearable item 100 delivers nutrients 102 to a small, targeted surface area of the body (e.g., a portion of a bicep). The wearable item 100 may also deliver different nutrients 102A, 102B to different areas of the body. While some nutrients 102A, 102B can penetrate the skin and reach the bloodstream within approximately 20 seconds of application, other nutrients 102A, 102B may take longer to pass through the skin. In exemplary embodiments, the wearable item 100 is able to place these nutrients 102A, 102B into the bloodstream within one minute, and at concentrations that the effects of the nutrients 102 last for several hours. While a shirt 100 is shown in FIG. 1 as the wearable item 100, other types of wearable items 100 can be used, e.g., hats, sweatbands, sweaters, jackets, pants, underwear, socks, watches, or any other wearable item that contacts the skin.

Figure 2:
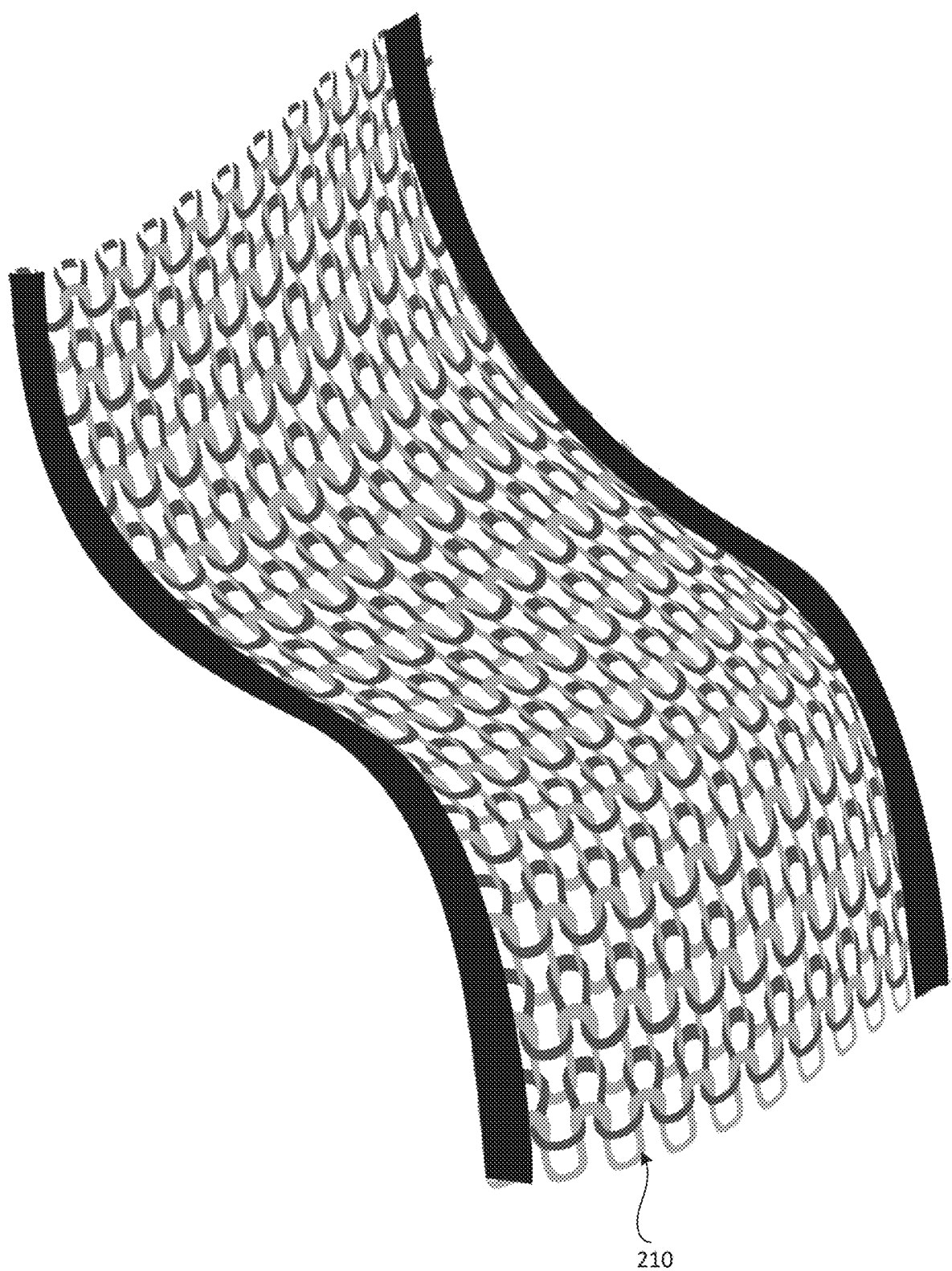
FIG. 2 illustrates an exemplary layout of moisture wicking fibers incorporated into the wearable item of FIG. 1B.

In some embodiments, in addition to delivering nutrients 102A, 102B transdermally using electroporation, the wearable item 100 can also protect the skin from harmful bacteria and germs. For example, this can be achieved by incorporating anti-microbial particles and/or antibacterial materials in the wearable item 100. In some embodiments, the wearable item 100 can also include material that protects the user from ultraviolet (UV) rays. The wearable item 100 may also include moisture-wicking fibers 210, as shown in FIG. 2, which remove sweat and water molecules that could possibly limit the effects of electroporation and/or interfere with the electrical circuitry of the wearable item 100. Furthermore, in some embodiments, the color of the wearable item 100 is based on photonic cells that produce their colors with reflective light rays (e.g., similar to butterflies using cellular produced color that holds no true dyed pigmentation but rather only reflective colors).

Figure 1B:
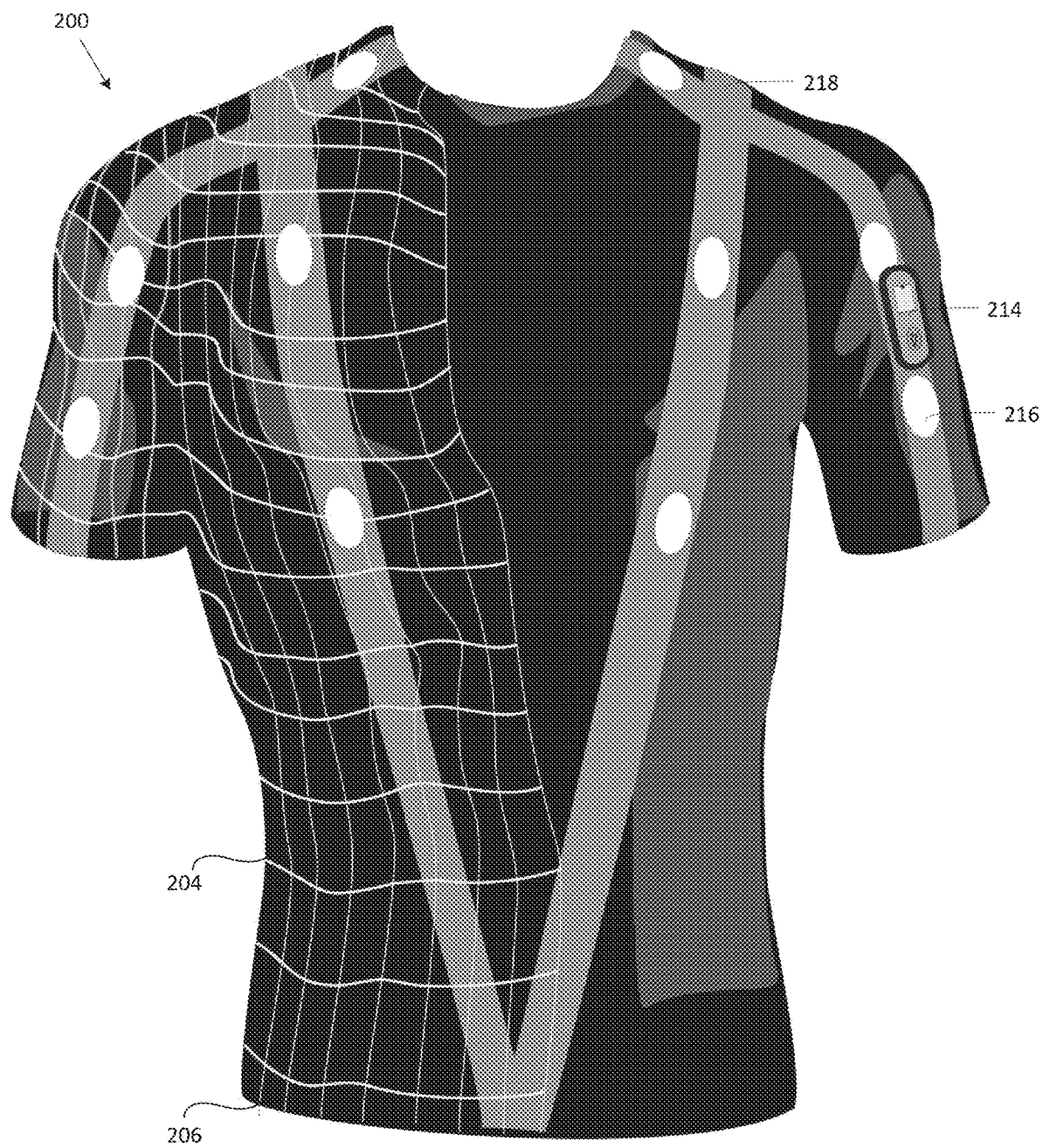

FIG. 1B illustrates another exemplary wearable item 200 in accordance with embodiments of the present disclosure. In addition to the functionality of the wearable item 100 shown in FIG. 1A, the wearable item 200 shown in FIG. 1B includes biometric sensors 216 that can measure various parameters of the user of the wearable item 200. The biometric sensors can include, but are not limited to, heart rate sensors, stress sensors, temperature sensors, breathing pattern sensors, activity sensors, calories sensors, sleep sensors, and electromyography sensors. This information can then be transmitted along a fabric circuit board 218 to a dongle 214. The dongle 214 is described in more detail in FIGS. 17-18C below. While nutrients are not shown in FIG. 1B, they are embedded within the plurality of non-conductive fibers 204.

Figure 3:
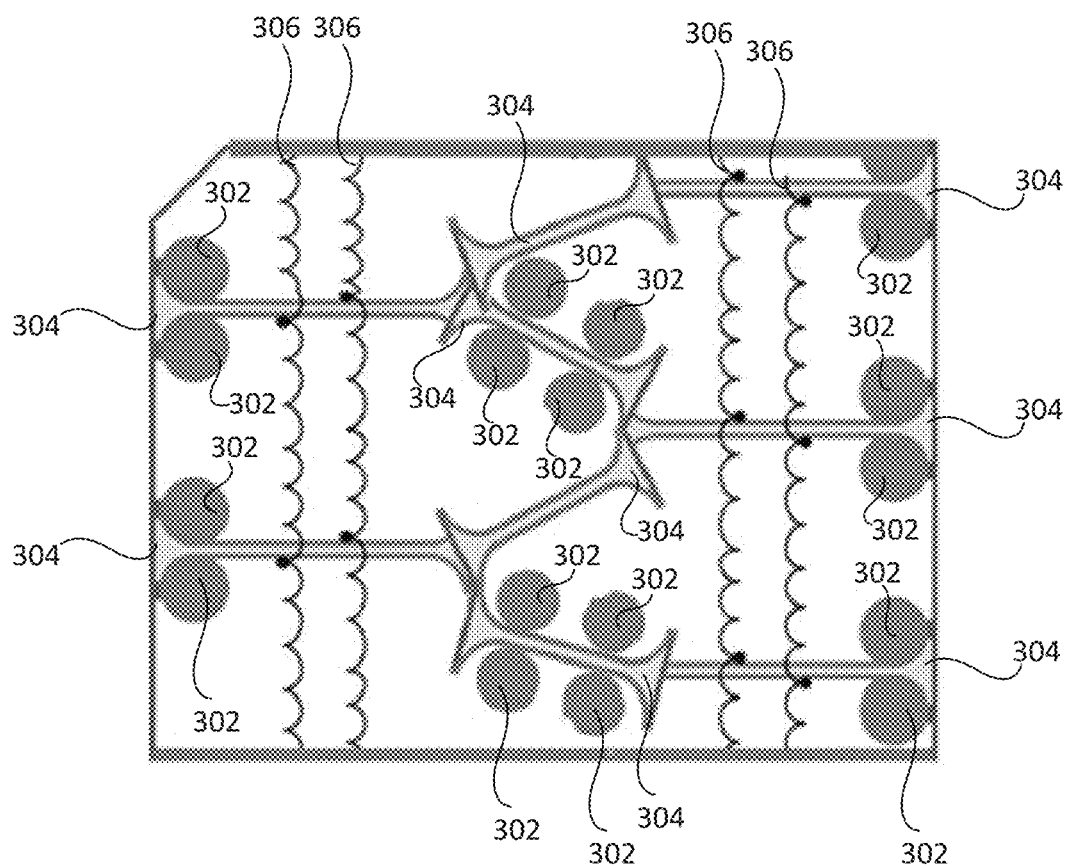
FIG. 3 illustrates an exemplary layout of the non-conductive fibers, conductive fibers, and nutrients within the wearable item of FIG. 1B.

As stated above, in some embodiments, the wearable item (100 in FIG. 1A, 200 in FIG. 1B) comprises a plurality of non-conductive fibers (104 in FIG. 1A, 204 in FIG. 1B), a plurality of conductive fibers (106 in FIG. 1A, 206 in FIG. 1B) interwoven with the plurality of non-conductive fibers (104 in FIG. 1A, 204 in FIG. 1B), and nutrients (102A, 102B in FIG. 1A) embedded within the plurality of non-conductive fibers (104 in FIG. 1A, 204 in FIG. 1B). FIG. 3 illustrates an exemplary layout of non-conductive fibers 304, conductive fibers 306, and nutrients 302 within a wearable item (e.g., the wearable item 100 in FIG. 1A or the wearable item 200 of FIG. 1B). The materials forming the non-conductive fibers 304 may be selected for properties relating to the retention and/or application of nutrients 302 to a user, in addition to properties relating to comfort or performance. For example, in some embodiments, the non-conductive fibers in the wearable item are at least one of the following types of fibers: bamboo fibers, ramie fibers, hydrophobic cotton fibers or hydrophilic cotton cellulose fibers.

The materials forming the conductive fibers 306 may be selected for their conductivity and their flexibility, so that the wearable item is able to conduct electricity while still being able to flex and conform to a user's body. For example, in some embodiments, the conductive fibers 306 are formed from a flexible material (e.g., bamboo fibers, ramie fibers, cotton strands, nylon strands or the like) dipped in a conductive material, thereby making the fibers into conductive fibers. The conductive materials can include, but are not limited to, copper, silver, gold, and the like. In some embodiments, the conductive materials can also include semi-conductive materials. In some embodiments, the conductive material or the semi-conductive material can include a small amount of elastane. In addition to providing electroporation, the conductive fibers 306 can also serve as a component of larger electromechanical biometric processes (e.g., monitoring heart rate, stress, temperature, breathing patterns and transmitting this information to a processor), as described in more detail below.

In some embodiments, and as shown in, e.g., FIG. 1A, the conductive fibers 106 are coupled to a power source 110. The power source 110 provides an electrical pulse to the conductive fibers 106 to create an electric field around the conductive fibers 106. That electric field can then be applied to the skin of the user of wearable item 100. As described above, the electric field creates the electroporation effect that increases the permeability of the lipid bilayer of the membrane of the stratum corneum (the outer layer of the skin that acts as the primary barrier to transdermal delivery). The increased permeability of the user's skin allows nutrients 102A, 102B to pass into the blood stream more effectively. As a result, a wearer may rapidly notice the physiological effects of the nutrients 102A, 102B (e.g., within minutes to hours).

In some embodiments, the power source 110 that supplies the electrical pulse to the conductive fibers 106 is a battery, such as a chemical battery or a bio-battery. In other embodiments, the power source 110 can be a circuit element that is charged from photovoltaic cells that are incorporated on the surface of the power source 110. Alternatively or additionally, the photovoltaic cells (i.e., solar cells) can be incorporated on the surface of the wearable item 100. In some embodiments, the photovoltaic cells can be ultraviolet (UV) reactive cells. In some other embodiments, the photovoltaic cells can be integrated into the fibers of the wearable item 100. In embodiments where photovoltaic cells are incorporated in the power source 110 and/or the wearable item 100, after the power source 110 stores enough energy, the stored energy can be discharged in the conductive fibers 106 to provide electroporation to the user's skin.

Figure 4:
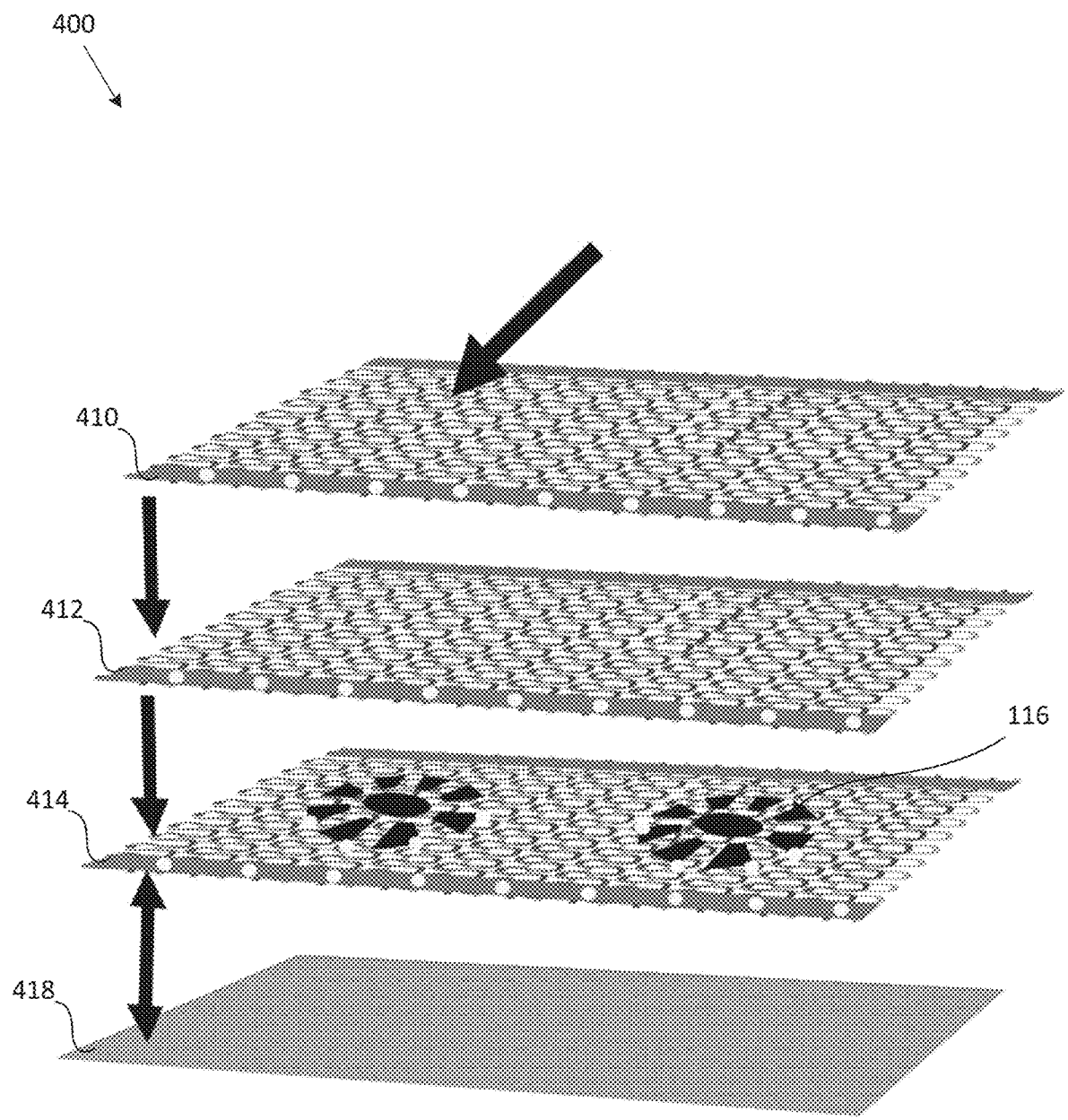
FIG. 4 illustrates an exemplary layout of multiple fiber layers that can be incorporated in the wearable item of FIG. 1B.

In some embodiments, and as shown in FIG. 4, a wearable item 400 has multiple layers of fabric material. For example, in some embodiments, a top layer 410 is comprised of bamboo fibers integrated with UV reactive particles (for conducting electricity) and silver or carbon particles, thereby providing the top layer of the wearable item 400 with conductive fibers. As also shown in FIG. 4, a middle layer 412 includes at least one of the following types of non-conductive fibers: bamboo fibers, ramie fibers, hydrophobic cotton fibers or hydrophilic cotton cellulose fibers. In some embodiments, the middle layer includes encapsulated nutrients (e.g., 102A and/or 102B in FIG. 1A). The third layer 414, disposed proximate to or adjacent the user's skin 618, includes biometric sensors 416. The layers 410, 412, 414 are held together with vertical strands of conductive fibers (not shown) and can be sewn together using computerized knitting technology in order to arrange the layers together in a fabric circuit board pattern that is capable of producing an electric field, using the power source 110, of about 25 V/m to about 125 V/m near the user's skin.

Referring back to FIG. 1A, the nutrients 102A, 102B embedded within the plurality of non-conductive fibers 104 are applied topically to the user of the wearable item 100. In some embodiments, the nutrients 102A, 102B include a first nutrient type 102A and a second nutrient type 102B. In some embodiments, the first nutrient type 102A and the second nutrient type 102B are embedded in the same regions of the wearable item 100. In other embodiments, the first nutrient type 102A and the second nutrient type 102B are embedded in a first region and a second region of the wearable item 100, respectively, wherein the first region is different than the second region. This arrangement of nutrients 102 can be useful in circumstances where the first region of the user's body needs different nutrients than the second region of the user's body. And, as a result, the first region can be targeted with a first nutrient type 102A while the second region can be targeted with a second nutrient type 102B.

Examples of nutrients 102A, 102B can include, but are not limited to, the following: amino acids, antioxidants, BCAA's, botanical products, carbohydrates, Creatine, Digestive Enzymes, Enzymes, Essential Fatty Acids, Fat-soluble Vitamins, Fiber, Glutamine, Herbal products, Macrominerals Minerals, Phytomedicines, Prescription Medications, Proteins, Testosterone, Trace minerals, Water-soluble Vitamins, Acai, Aloe Vera, Alpha-Tocopherol, Artichoke Astaxanthin, Astragalus, Baicalin, Bilberry, Bitter Orange, Black Cohosh, Botanical Dietary Supplements, Bromelain, Butterbur, Caffeine, Calcium, Cat's Claw, Chamomile, Chasteberry, Choline, Chromium, Cinnamon, Coenzyme CoQ10 (QH), Collagen, Copper, Cranberry, Dandelion, Echinacea, EPA/DHA, Ephedra, Essiac/Flor-Essence, European Elder, Evening Primrose Oil, Fenugreek, Feverfew, Flaxseed/Flaxseed Oil, Folate, Garlic, Gelatin, Ginger, Ginkgo, Ginseng, Glucosamine (Sulfate), Chondrotin, Glutathione, Goldenseal, Grape Complex, Grape Seed Extract, Green Tea, Green Tea Extract, Hawthorn, Herbal Dietary Supplements, Hoodia, Horse Chestnut, Huperzine A, Hyaloronic Acid, Iodine, Iron, Kava, Lavendar, Leucoanthocyanins, Licorice Root, Lignans, Lutein, Lycopene, Magnesium, Milk Thistle, Mistletoe, Multivitamin/mineral Supplements, Nitric Oxide, Noni, Olive Leaf, Olive Oil/Fruit, PC-SPES, Peppermint Oil, Phytic Acid, Polyphenols, Pomegranate, Proanthocyanidins, Proline, Quercetin, Red Clover, Sage, SAMe, Saw Palmetto, Selenium, Selenium, Soy, St. John's Wort, Tea, Thiamin, Thunder God Vine, Tocotrienols, Tretinoin Vitamin A, Turmeric, Valerian, Vitamin A, Vitamin B1, Vitamin B12, Vitamin B6, Vitamin C, Vitamin D, Vitamin E, Vitamin E—Isomer E, Vitamin K, Yohimbe, and Zinc.

Figure 5:
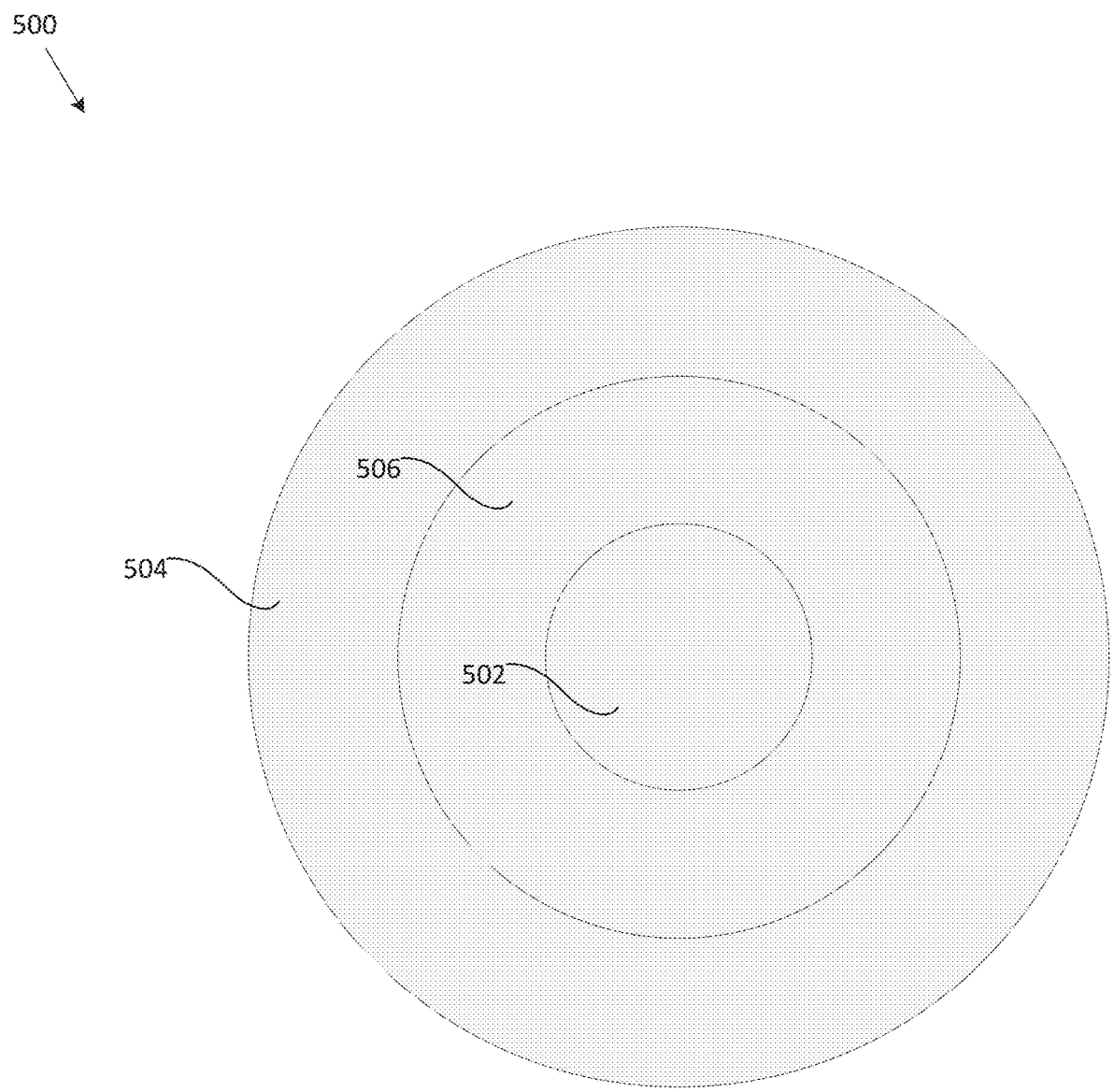
FIG. 5 depicts an exemplary encapsulated nutrient, according to embodiments of the present disclosure.

In some embodiments, the nutrients 102A, 102B can be encapsulated in order to aid the nutrients 102A, 102B in bypassing the epidermal skin layer and to target specific areas of body. FIG. 5 depicts an exemplary encapsulated nutrient 500, according to the embodiments of the present disclosure. An encapsulated nutrient 500 includes a capsule 504 that encloses a vesicle 506 in which a nutrient 502 is stored. The vesicle 506 is released from the capsule 504 and passes through the skin, where it delivers the enclosed nutrient into the bloodstream while the capsule 504 remains embedded within the wearable item (e.g., the wearable item 100 in FIG. 1A). The use of particular nutrients 502 (e.g., vitamin B-12 and other water-soluble vitamins) can involve special vesicles 506 for encapsulating the nutrients 502. In some embodiments, the capsules 504 are placed in proximity to conductive fibers (e.g., conductive fibers 106 in FIG. 1A) so that the electric current on the conductive fibers can help to disperse the vitamins from the capsules 504.

Figure 6:
FIG. 6 illustrates an exemplary vitamin level and charge indicator that is incorporated in the wearable item of FIG. 1B.
Figure 7A:
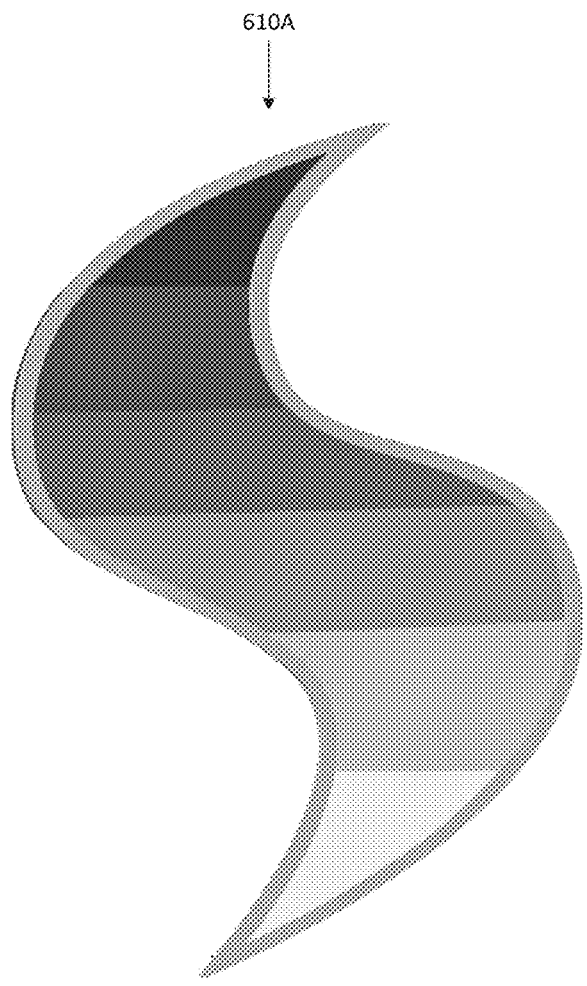
FIGS. 7A-7B depict different indication levels of the vitamin level and charge indictor illustrated in FIG. 6.
Figure 7B:
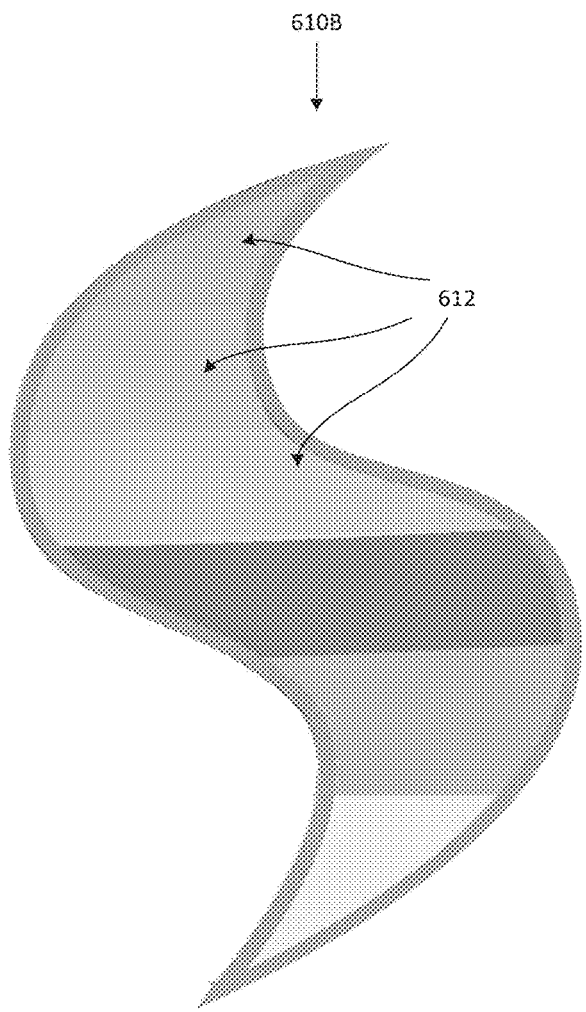

As the wearable item 100 is utilized, the nutrients 102A, 102B embedded within the wearable item 100 and the charge stored in the power source 110 decrease. In exemplary embodiments, the wearable item 100 includes a vitamin level and charge indicator 610, as shown in FIG. 6. FIGS. 7A-7B depict how vitamin levels and charge indictors 610A, 610B change depending on the levels of nutrients embedded within the wearable item and the charge of the power source. In particular, the vitamin level and charge indicator 610A in FIG. 7A indicates that the level of nutrients embedded within the wearable item and the charge in the power source are full. In contrast, the vitamin level and charge indicator 610B in FIG. 7B indicates that the level of nutrients embedded within the wearable item and the charge in the power source are half full. That is, the first three levels 612 of the vitamin level and charge indicator 610 are greyed out. When the nutrients and the charge in the power source are fully exhausted, the entire vitamin level and charge indicator 610B will be greyed out.

In embodiments where the power source is fully depleted, the power source can be connected to an external power source, using a power cord, Universal Serial Bus (USB) connector and the like.

In embodiments where the nutrients of wearable item are exhausted, the wearable item may be submerged in a replenishing and strengthening solution (referred to as a "washing solution"). The concentration of nutrients/capsules in the washing solution may vary. For example, in some situations the concentration may be higher to decrease soaking time needed for adequate replenishing; in other situations the concentration may be lower to prevent degeneration of the fibers of the wearable item. In embodiments where the nutrients are encapsulated nutrients (e.g., as shown in FIG. 5), the washing solution can include nutrients 502 that become encapsulated in existing capsules 504 in the wearable item or may include new capsules 504 that attach to the wearable item. Any active electric components of the wearable item (e.g., the chip as discussed below) may be incorporated into a waterproof container to prevent damage during soaking. The replenishing and strengthening solution may be incorporated into a laundry detergent.

In some embodiments, the washing solution includes components that reinforce and replenish the conductivity of the conductive fibers of the wearable item. For example, the washing solution can include silver particles that will recoat the conductive fibers with silver, thereby increasing the conductivity of the wearable item. In some embodiments, the washing solution is designed to be safe in a regular washing cycle and is phosphate & paraben free. The washing solution can also include color changing technology that will change the color of the wearable item when the wearable item is washed in the washing solution.

Figure 8:
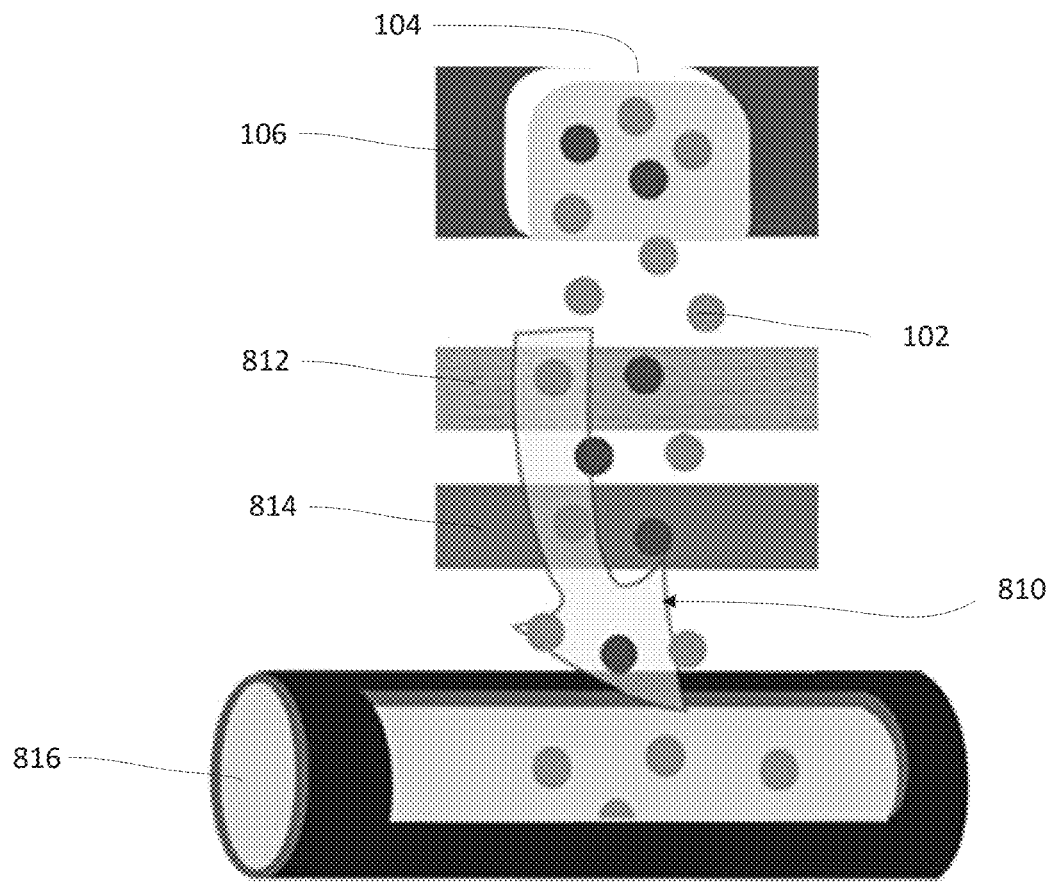
FIG. 8 illustrates an exemplary diagram of an electrical field being applied to a user's skin, according to embodiments of the present disclosure.

As stated above, the plurality of conductive fibers (e.g., the conductive fibers 106 in FIG. 1A) are configured to apply an electric field to a portion of the skin of a user wearing the wearable item (e.g., the wearable item 100 in FIG. 1A), thereby increasing the permeability of the portion of the skin with respect to the nutrients (e.g., nutrients 102A, 102B in FIG. 1A). FIG. 8 illustrates an exemplary diagram of an electrical field 810 being applied to a user's skin (epidermis 812 and dermis 814) of the wearable item 100. In exemplary embodiments, the electrical field 810, generated by the conductive fibers 106, is approximately perpendicular to the epidermis 812 and dermis 814 of the user's skin. In these embodiments, the electroporation of the user's epidermis 812 and dermis 814 is particularly effective. In other embodiments, the electrical field 810 is applied at an angle other than perpendicular to the user's epidermis 812 and dermis 814. After the electrical field 810 is applied nutrients 102 can be transported to the blood stream 816 of the user.

In some embodiments, the strength of the electric field produced by the power source (e.g., power source 110 in FIG. 1A) can be a range of about 25 V/m to about 125 V/m. This electric field strength will achieve sufficient electroporation to enable the entry of the microencapsulated energy blend across the stratum corneum. In some embodiments, the conductive fibers (e.g., conductive fibers 106 in FIG. 1A) are arranged in a pattern similar to a Marx generator (that in some embodiments can be similar to the arrange of an electrical organ in an electric eel), which will enable the amplification of the electric field of the conductive fibers 106 and thereby generate electric fields from 25 V/m to 125 V/m.

In exemplary embodiments, in addition to providing an electric field 810 to the skin of the user for electroporation, the conductive fibers 106 can also be configured to provide an electric field that aids in the transport of the encapsulated nutrients 500. For example, in these embodiments, the encapsulated nutrients 500 can be electrically charged. When an electric field is applied to the encapsulated nutrients 500, the encapsulated nutrients 500 are accelerated into the blood stream of a user after the electroporation of the epidermis 812 and dermis 814 of the user's skin. This accelerates the absorption of the nutrients 502 by the user.

Figure 9A:
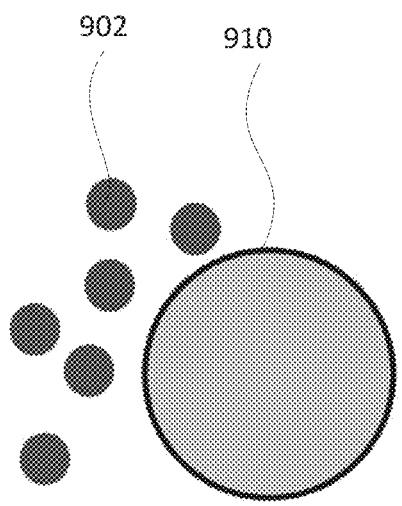
FIGS. 9A-9C depict the transformation of a user's skin as it undergoes electroporation, according to embodiments of the present disclosure.
Figure 9B:
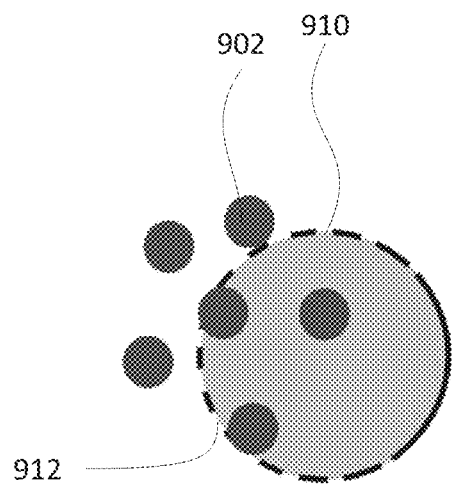
Figure 9C:
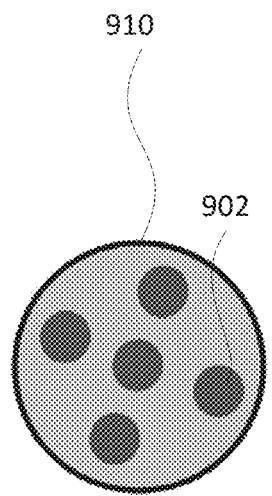

FIGS. 9A-9C depict the transformation of a user's skin as it undergoes electroporation. In particular, FIG. 9A depicts a user's skin 910 before an appropriate electric field (e.g., 25 V/m-125 V/m) is applied to the user's skin 910. Without electroporation of the user's skin 910, nutrients 902 are unable to penetrate the user's skin 910. After an appropriate electric field is applied, however, the pores of the user's skin 910 open up so that the nutrients 902 can penetrate the user's skin 910, as shown in FIG. 9B. After the nutrients 902 are absorbed by the user's skin 910 the application of the electric field to the user's skin can be discontinued and the pores 912 will no longer be present in the user's skin, as shown in FIG. 9C.

Figure 10:
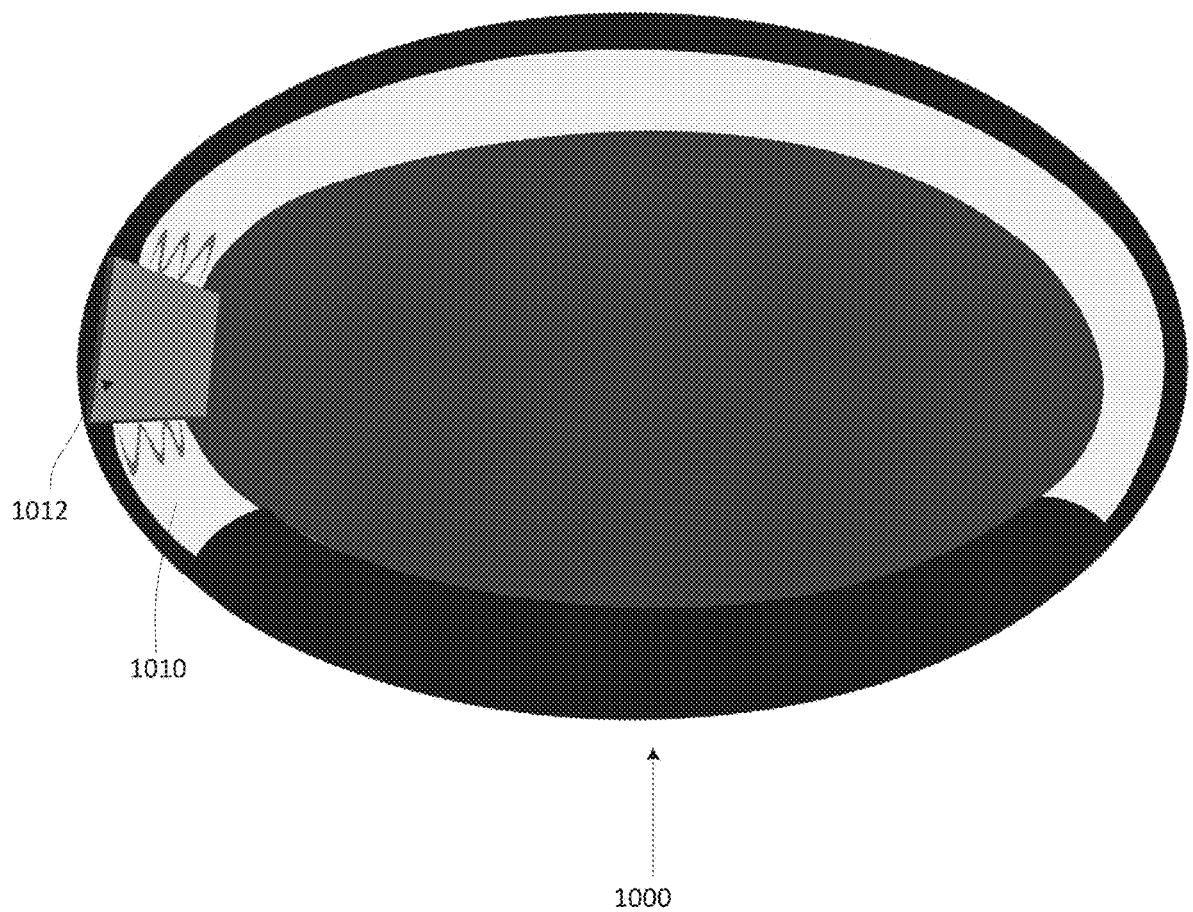
FIG. 10 illustrates an exemplary fit-adjusting strap, according to embodiments of the present disclosure.
Figure 11:
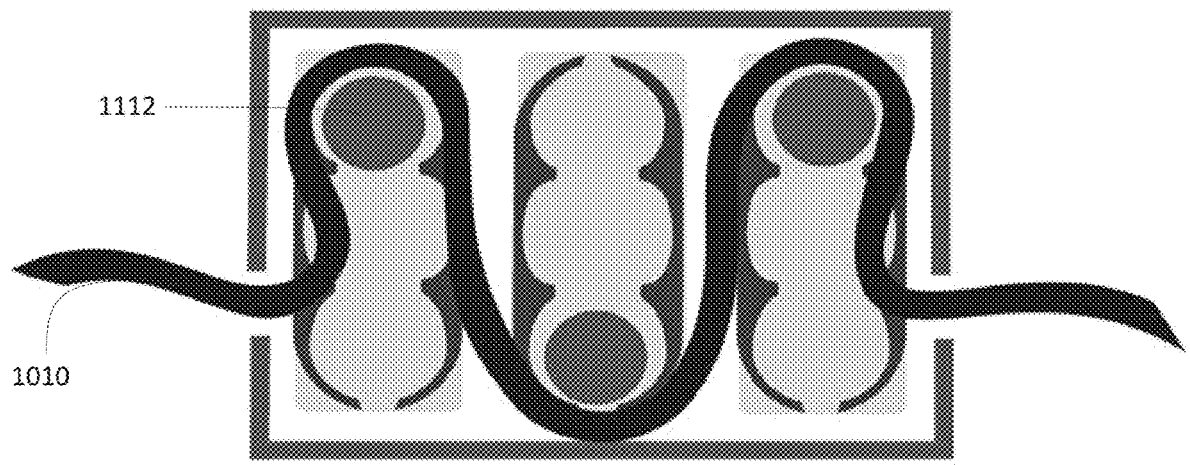
FIG. 11 illustrates an exemplary adjusting mechanism for the fit-adjusting strap illustrated in FIG. 10.
Figure 12:
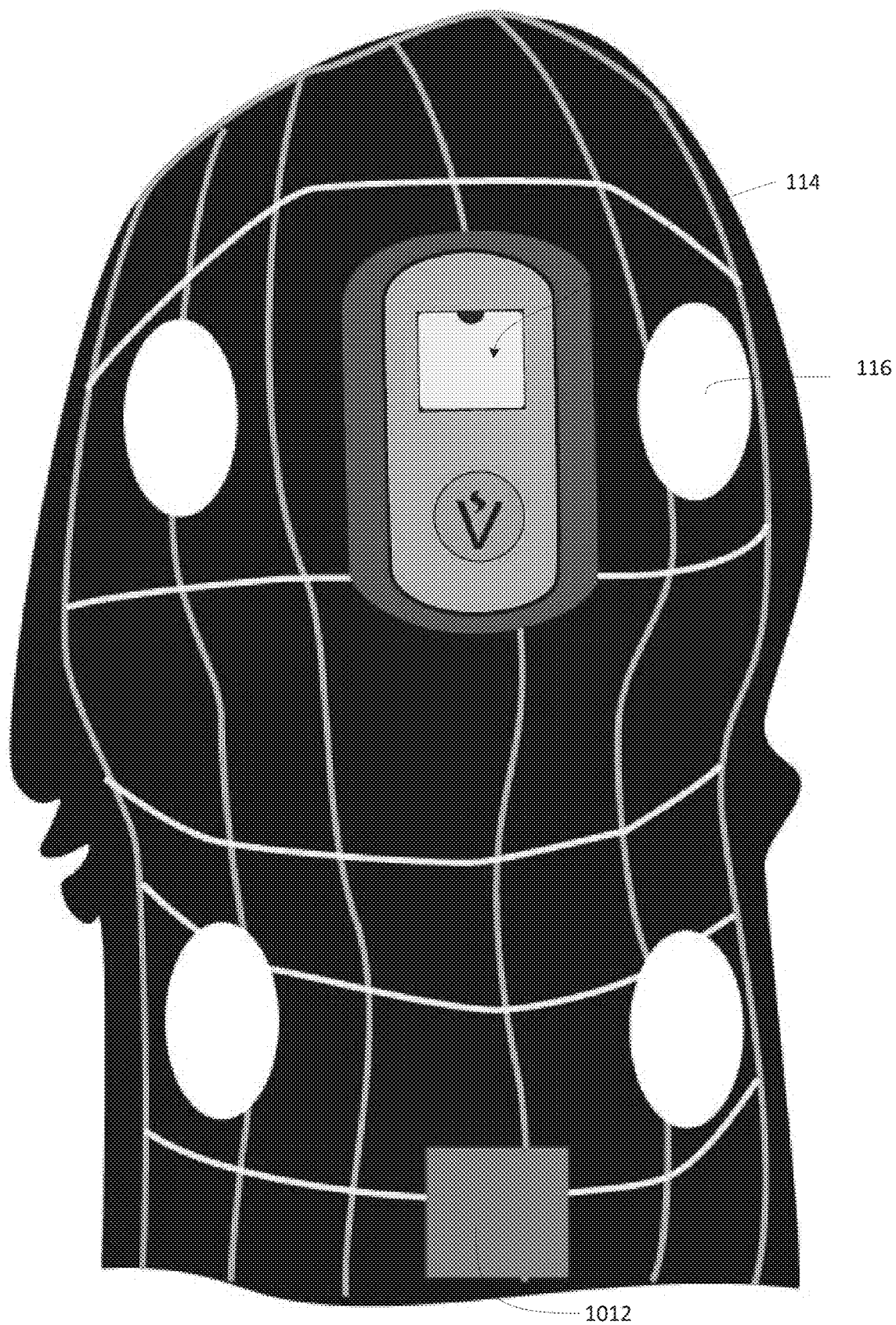
FIG. 12 illustrates an exemplary fit-adjusting strap integrated in the wearable item of FIG. 1B.

In exemplary embodiments, since the electrical field decreases at a rate of $1/r^2$, the wearable item should be close to the wearer's skin. In some embodiments, this can be achieved customizing the wearable item to the user's shape. In embodiments where customizing the wearable item may not be feasible, the wearable item can include a fit-adjusting strap 1010, as shown in FIG. 10. FIG. 10 illustrates a top-down view of the fit-adjusting strap 1010. The fit-adjusting strap 1010 can include a fit adjusting button 1012 that, when pressed, will pull the wearable item 1000 taut around the user. In some embodiments, the fit adjusting strap 1010 can be woven between alternating bars 1112, as shown in FIG. 11. Then, when the fit adjusting button 1012 is pressed, the wearable item 1000 will tighten on the user by aligning the alternating bars 1112 and pulling the excess material of the wearable item 1000 taut. This will allow the electrical field 810 to be applied more closely to the user's skin. In these embodiments, the flexibility of the conductive fibers and other materials enables the customization of the wearable item 1000 to the user. In some embodiments, multiple fit-adjusting straps 1010 can be included in the wearable item 1000, such as the waist, the sleeves (shown in FIG. 12), and the chest.

Figure 13:
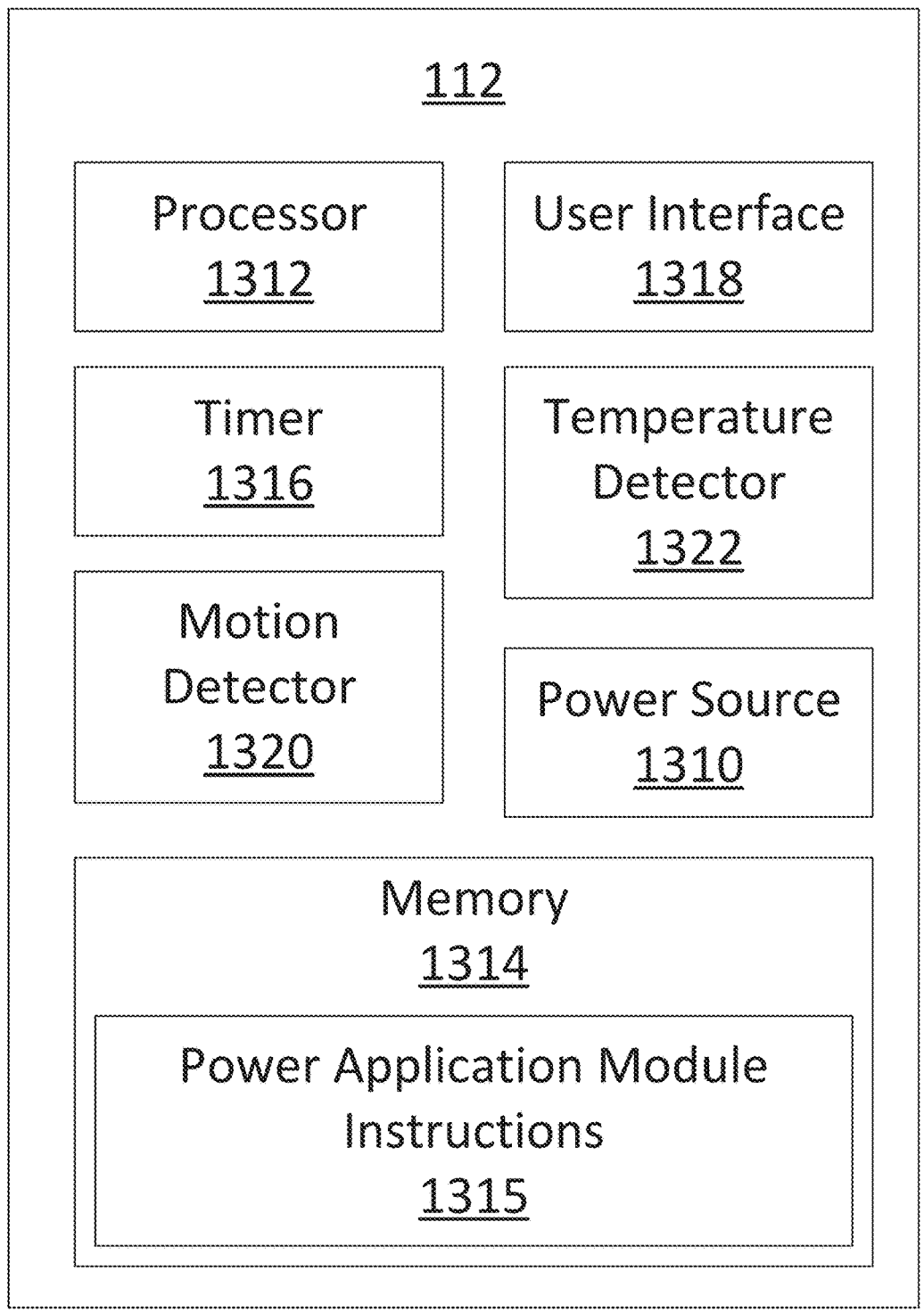
FIG. 13 illustrates an exemplary processor-based nutrient applicator, according to the embodiments of the present disclosure.

As stated above, the wearable item 100 in FIG. 1A includes a processor-based nutrient applicator 112. FIG. 13 illustrates an exemplary processor-based nutrient applicator 112 that includes power application module instructions 1315 stored on memory 1314. The power application module instructions 1315 instruct the processor-based nutrient applicator 112 to perform one, multiple, or all of the functions described above and below. For example, in some embodiments, the processor-based nutrient applicator 112 is configured to apply voltages to conductive fibers 106 for electroporation. In embodiments where different nutrients 102A, 102B are embedded at different locations in the wearable item 100, the processor-based nutrient applicator 112 can be configured to apply voltages (either automatically or through user input) to different sets of conductive fibers 106 at different locations at different times. In this manner, the wearable item 100 may selectively increase the application of any one or a combination of different nutrients 102 at different rates. In embodiments where the nutrients 102A and/or 102B are encapsulated nutrients 500, the electric field needed to release the nutrients 502 from the capsules 504 can be greater than the electric field needed for adequate electroporation. In these embodiments, the processor-based nutrient applicator 112 is programmed to apply a voltage level to the conductive fibers 106 for a predetermined time period that is sufficient for electroporation. After the predetermined time period, the processor-based nutrient applicator 112 increases the voltage to release the nutrients 502 from the capsules 504. In embodiments where the electric field needed to release the nutrients 502 from the capsules 504 is less than the electric field needed for adequate electroporation, the processor-based nutrient applicator 112 may apply a voltage to certain conductive fibers 106 located remote from the capsules 704 for electroporation before applying the electric field to other conductive fibers 106 located proximate to capsules 504 to release the nutrients 502 from the capsules 504. In some embodiments, the process-based nutrient applicator 112 can be configured to receive energy from conductive fibers 106 in the wearable item 100.

The processor-based nutrient applicator 112 can include a power source 1310. In some embodiments, the power source 1310 can be the same power source 110 as described above and can be coupled to and/or incorporated into the processor-based nutrient applicator 112 to power the processor-based nutrient applicator 112.

According to various embodiments, the processor-based nutrient applicator 112 may include any one or all of the modules shown in FIG. 13. For example, the processor-based nutrient applicator 112 may include a processor 1312 and memory 1314 (which may be a tangible, non-transitory storage medium such as flash memory or DRAM). The processor 1312 may execute power application module instructions 1315 stored on the memory 1314 in order to selectively apply a voltage to conductive fibers (e.g., conductive fibers 106 in FIG. 1A). The power application module instructions 1315 can include instructions to determine when to apply voltages, to which conductive fibers 106 the voltage is applied, and for how long the voltage is applied. The power application module instructions 1315 may include timing instructions to regulate when and for how long the power source applies the voltage to the conductive fibers. Additionally, the power application module instructions 1315 can include instructions to selectively apply a first electric field to the user's skin to increase the permeability of the user's skin with respect to nutrients of a first type (e.g., nutrients 102A in FIG. 1A) and to selectively apply a second electric field to the user's skin to increase the permeability of the user's skin with respect to nutrients of a second type (e.g., nutrients 102B in FIG. 1A). The memory 1314 can also include any instructions necessary to complete any of the other functions described above and below.

The processor-based nutrient applicator 112 may include a user interface 1318 through which the user may receive information from or provide information to the processor 1312 or memory 1314. For example, the user interface 1318 may incorporate a touch screen or may be a simple button. A user interacts with the user interface 1318 in some embodiments to activate the voltages applied by the power source to the conductive fibers or to alter the amount or duration of the voltages. The user may further program the processor-based nutrient applicator 112 to apply certain voltages at certain times.

In some embodiments, the processor-based nutrient applicator 112 includes a motion detector 1320 (e.g., an accelerometer) and may also include a temperature detector 1322. The chip may further include a humidity detector, a light detector (e.g., a photodiode), and/or a GPS unit. Each of those components may be used to detect a particular condition or external environment, which may be used by the processor to trigger the application of voltages to the conductive wires. In some embodiments, responses, based on input from the motion detector 1320 and temperature detector 1322, can be elicited by the processor-based nutrient applicator 112 (e.g., a rhythmic playlist, nutrient application, and the like.)

Figure 14A:
FIG. 14A-14C illustrate exemplary dongles, according to embodiments of the present disclosure.

In exemplary embodiments, the processor-based nutrient applicator 112 can be incorporated into a dongle 114. FIG. 14A illustrates an exemplary dongle 114, according to the embodiments of the present disclosure. In addition to the functions performed by the processor-based nutrient applicator 112 above, in exemplary embodiments, the dongle 114 can be a depository for nutrient packs, include a user interface 1410, and include its own power source or be coupled to the power source 110 described above. The benefit of having a depository for nutrient packs is that some of the nutrients encapsulated on the wearable item can have a short shelf life (e.g., around two to five days). As a result, preservation and replenishment of the nutrients can be satisfied by storing the nutrients in a nutrient pack on the dongle 114. Then, when nutrients are needed by the user, the nutrients can be transported from the nutrient pack, upon activation of the dongle 114, to the appropriate location on the wearable item via pathways (e.g., cellular tubes). In some embodiments, the nutrients can be transported along the pathways by exposing the nutrients to an electric field and/or light pulse.

In exemplary embodiments, the dongle 114 can be removed from the wearable item. That is, the wearable item can comprise an interface configured to secure the removable dongle 114 to the wearable item and to control a proximity of the removable dongle 114 to the skin of the user.

Figure 14B:
Figure 14C:
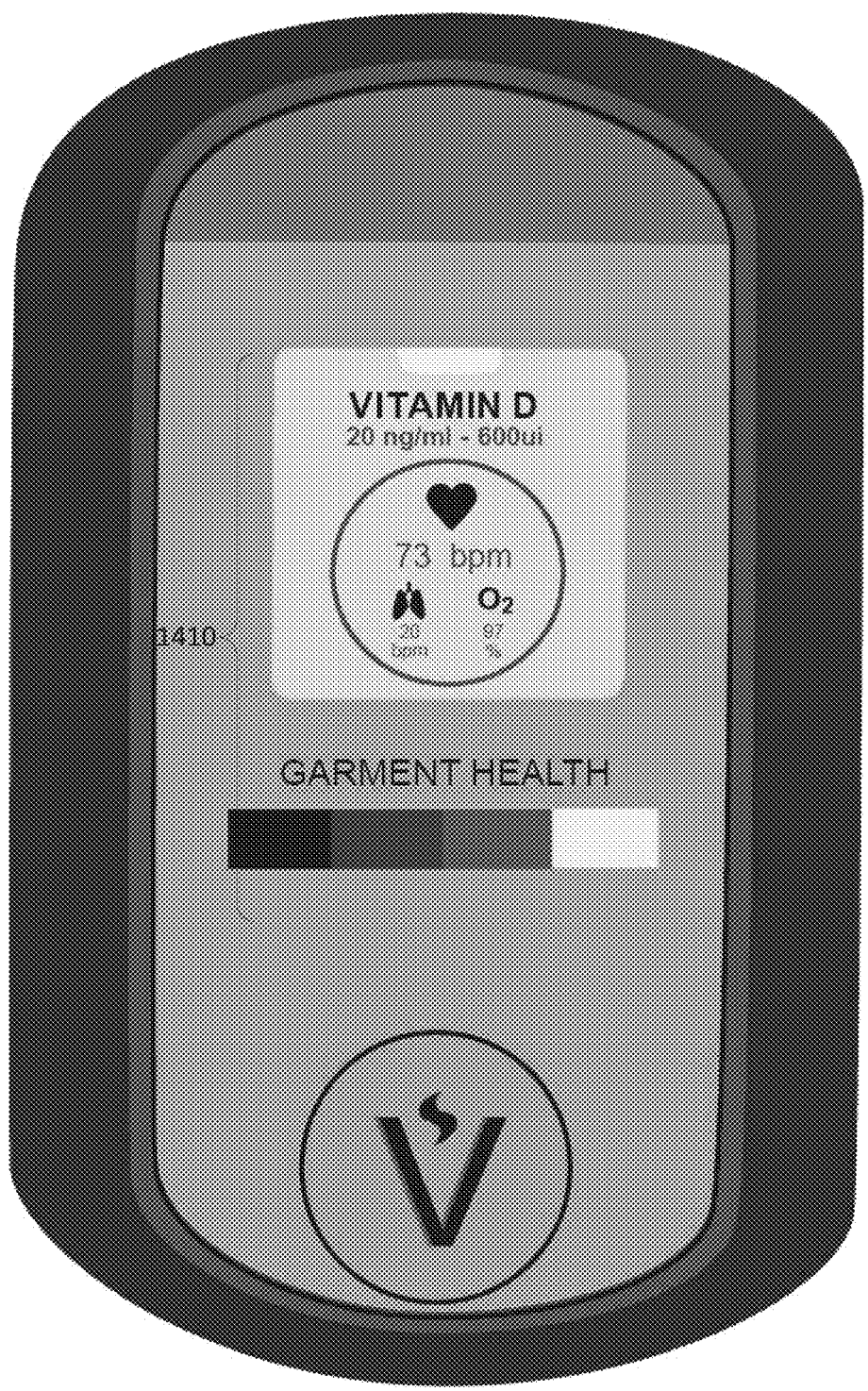
Figure 15:
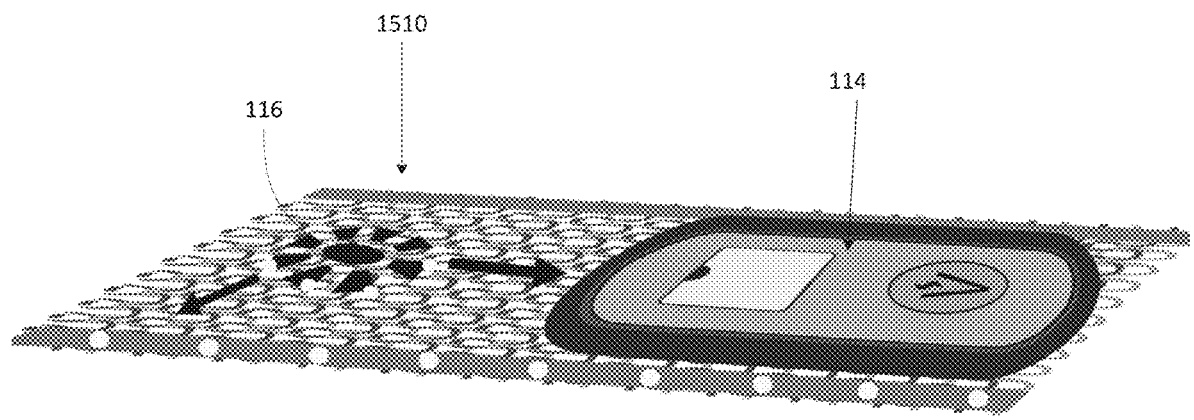
FIG. 15 illustrates an exemplary dongle and fibers for transporting the biometric information and electrical communication signals from the biometric sensors to the dongle.

In exemplary embodiments, the dongle 114 can include other functionality including, but not limited to, displaying biometric readings (e.g., heart rate, stress, temperature, breathing patterns of user) on the user interface 1410 (depicted in FIGS. 14A-14C), provide feedback based on the biometric monitoring (e.g., adapting music to the measured heartrate), interface with other smart devices (e.g., Fitbit, Apple Watch, etc.), provide Bluetooth and Wi-Fi compatibility (depicted in FIG. 14A), provide Global Positioning System (GPS) monitoring, provide notifications (e.g. notification of an incoming call to a user's cellular phone and depicted in FIG. 14B) and function as a music player (e.g., download songs to the dongle and listen to the songs via a headphone jack incorporated in the dongle 114 or via Bluetooth) (depicted in FIG. 14B). According to some embodiments, the dongle 114 can communicate with the biometric sensors 116 and other electronics along a network of conductive fibers 1410 of the wearable item 100, as shown in FIG. 14 and explained in FIG. 4 above.

In exemplary embodiments, other information displayed by the user interface 1410 includes the type of nutrients in the nutrient pack, the amount of nutrients left in the nutrient pack, how saturated the wearable item is with nutrients (depicted in FIGS. 14A-14C), whether the conductive fibers are conducting electricity efficiently, the remaining useful life of the wearable item (depicted in FIG. 14C), the amount of energy available to the power application module for electroporation, whether the wearable item has been damaged, biometric feedback from biometric sensors incorporated in the wearable item (e.g., heart rate, blood-oxygen level, etc.), whether Bluetooth is enabled, whether Wi-Fi is enabled, a user interface for changing a song that the user is listening to (depicted in FIG. 14B), and the like.

Figure 16:
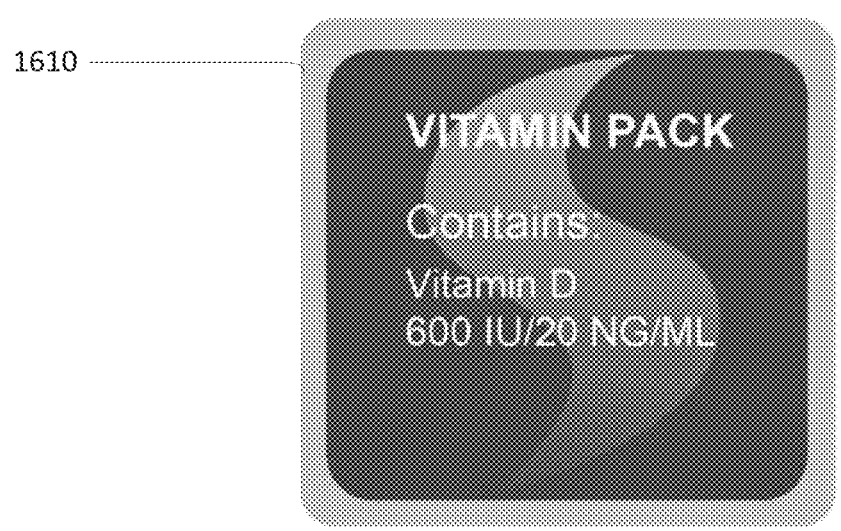
FIG. 16 illustrates an exemplary vitamin pack, according to embodiments of the present disclosure.

FIG. 16 illustrates an exemplary vitamin pack 1610. The vitamin pack 1610 can include a description of the type of vitamin that is stored in the vitamin pack 1610 (Vitamin D in this particular example) and the amount of vitamins in the vitamin pack 1610 (600 International Units (IU) in this particular example).

Due to the embodiments described above, the wearable item (e.g., the wearable item 100 in FIG. 1A) can be used to replenish nutrients (e.g., nutrients 102A, 102B in FIG. 1A) consumed during exercise and/or provide essential nutrients in those who are facing malnutrition. In this manner, the wearable item may be used to combat health challenges posed by nutritional deficiencies. Additionally, in some embodiments, delivery of vitamins directly to the bloodstream by way of safe electroporation methods will eliminate negative effects presented by energy-stimulating products such as gastro-intestinal distress, water imbalance, and absorption of unwanted compounds such as excess sugar or artificial sweeteners, which are found in many energy-enhancing products on the market. Furthermore, in some embodiments, delivery of vitamins to the bloodstream can provide hospital patients an alternative to having to swallow prescribed medicine or for soldiers in the field requiring immediate nutritional support.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive. That is, various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A wearable item for applying nutrients to a user, the wearable item comprising:
   a plurality of non-conductive fibers;
   nutrients embedded within the plurality of non-conductive fibers;
   a plurality of conductive fibers interwoven with the plurality of non-conductive fibers and formed into an item configured to be worn by a user, the plurality of conductive fibers being configured to apply an electric field from about 25 V/m to about 125 V/m to a portion of the skin of a user wearing the wearable item to induce an electroporation effect and thereby increase a permeability of the portion of the skin with respect to the nutrients; and
   a processor-based nutrient applicator configured to selectively apply a voltage to the plurality of conductive fibers to cause the plurality of conductive fibers to apply the electric field to the skin of the user, the processor-based nutrient applicator comprising a motion detector configured to trigger application of the voltage to the plurality of conductive fibers and thereby cause the plurality of conductive fibers to apply the electric field to the skin of the user.

2. The wearable item of claim 1, wherein the nutrients are selected from a group consisting essentially of: water-soluble vitamins and fat-soluble vitamins.

3. The wearable item of claim 1, wherein the plurality of non-conductive fibers include at least one of the following: bamboo fibers, ramie fibers, hydrophobic cotton fibers or hydrophilic cotton cellulose fibers.

4. The wearable item of claim 1, wherein the nutrients include a first nutrient type and a second nutrient type, and the nutrients of the first nutrient type are embedded within a first region of the wearable item and the nutrients of the second nutrient type are embedded within a second region of the wearable item, wherein the first region is different than the second region.

5. The wearable item of claim 1, wherein the processor-based nutrient applicator is a removable dongle, and wherein the wearable item further comprises an interface configured to secure the removable dongle to the wearable item and to control a proximity of the removable dongle to the skin of the user.

6. The wearable item of claim 1, further comprising a visual indicator configured to convey information regarding an amount of nutrients coupled to the plurality of non-conductive fibers.

7. The wearable item of claim 1, wherein the plurality of conductive fibers are flexible.

8. The wearable item of claim 1, wherein the nutrients are enclosed in vesicles.

9. The wearable item of claim 8, wherein the electric field is configured to disperse the nutrients from the vesicles.

10. The wearable item of claim 1, wherein the processor-based nutrient applicator is configured to selectively apply (A) a first voltage to the plurality of conductive fibers to cause the plurality of conductive fibers to induce the electroporation effect and (B) a second voltage to the plurality of conductive fibers to cause the plurality of conductive fibers to induce nutrient release, the second voltage being greater than the first voltage.

11. The wearable item of claim 5, wherein the interface is a first interface, and wherein the removable dongle comprises a user interface configured to display at least one of an amount of nutrients carried by the wearable item, an amount of energy available to the wearable item for inducing the electroporation effect, and user biometric data.

12. A wearable item for applying nutrients to a user, the wearable item comprising:
   a plurality of non-conductive fibers;
   nutrients embedded within the plurality of non-conductive fibers; and
   a plurality of conductive fibers interwoven with the plurality of non-conductive fibers and formed into an item configured to be worn by a user, the plurality of conductive fibers being configured to apply an electric field from about 25 V/m to about 125 V/m to a portion of the skin of a user wearing the wearable item to induce an electroporation effect and thereby increase a permeability of the portion of the skin with respect to the nutrients;
   a processor-based nutrient applicator configured to selectively apply a voltage to the plurality of conductive fibers to cause the plurality of conductive fibers to apply the electric field to the skin of the user, wherein the processor-based nutrient applicator is a removable dongle; and
   a first interface configured to secure the removable dongle to the wearable item and to control a proximity of the removable dongle to the skin of the user;
   wherein the removable dongle comprises a user interface configured to display at least one of an amount of nutrients carried by the wearable item, an amount of energy available to the wearable item for inducing the electroporation effect, and user biometric data.

13. The wearable item of claim 12, wherein the nutrients are selected from a group consisting essentially of: water-soluble vitamins and fat-soluble vitamins.

14. The wearable item of claim 12, wherein the plurality of non-conductive fibers include at least one of the following: bamboo fibers, ramie fibers, hydrophobic cotton fibers or hydrophilic cotton cellulose fibers.

15. The wearable item of claim 12, wherein the nutrients include a first nutrient type and a second nutrient type, and the nutrients of the first nutrient type are embedded within a first region of the wearable item and the nutrients of the second nutrient type are embedded within a second region of the wearable item, wherein the first region is different than the second region.

16. The wearable item of claim 12, further comprising a visual indicator configured to convey information regarding an amount of nutrients coupled to the plurality of non-conductive fibers.

17. The wearable item of claim 12, wherein the plurality of conductive fibers are flexible.

18. The wearable item of claim 12, wherein the nutrients are enclosed in vesicles.

19. The wearable item of claim 18, wherein the electric field is configured to disperse the nutrients from the vesicles.

20. The wearable item of claim 12, wherein the processor-based nutrient applicator is configured to selectively apply (A) a first voltage to the plurality of conductive fibers to cause the plurality of conductive fibers to induce the electroporation effect and (B) a second voltage to the plurality of conductive fibers to cause the plurality of conductive fibers to induce nutrient release, the second voltage being greater than the first voltage.

* * * * *